United States Patent [19]

Ripley et al.

[11] Patent Number: 5,246,662
[45] Date of Patent: Sep. 21, 1993

[54] METHODS FOR GENERATING CHLORINE DIOXIDE AND COMPOSITIONS FOR DISINFECTING

[75] Inventors: Paul S. Ripley, Irvine; Anthony J. Dziabo, El Toro, both of Calif.; James P. Ringo, Norman, Okla.

[73] Assignee: Allergan, Inc., Irvine, Calif.

[21] Appl. No.: 969,549

[22] Filed: Oct. 30, 1992

Related U.S. Application Data

[60] Continuation of Ser. No. 765,219, Sep. 24, 1991, abandoned, which is a division of Ser. No. 416,074, Oct. 2, 1989, Pat. No. 5,078,908.

[51] Int. Cl.$^5$ .................. A61L 2/00; C01B 11/02
[52] U.S. Cl. ..................... 422/29; 422/37; 252/187.21; 252/187.23
[58] Field of Search ............ 422/29, 37; 435/267; 252/187.21, 187.23, 186.36

[56] References Cited

U.S. PATENT DOCUMENTS

| | | | |
|---|---|---|---|
| Re. 23,218 | 4/1950 | Levy | 252/187.23 |
| Re. 32,672 | 5/1988 | Huth et al. | 252/95 |
| 2,477,631 | 8/1949 | Levy et al. | 8/105 |
| 3,123,521 | 3/1964 | Wentworth | 167/17 |
| 3,278,447 | 10/1966 | McNicholas | 252/187.21 |
| 3,386,915 | 6/1968 | Rutschi | 424/661 |
| 3,563,702 | 2/1971 | Partridge | 252/187.23 |
| 3,585,147 | 6/1971 | Gordon | 252/187.23 |
| 3,591,515 | 7/1971 | Lovely | 252/187.21 |
| 3,910,296 | 10/1975 | Karageozian et al. | 252/174.12 |
| 3,912,451 | 10/1975 | Gaglia, Jr. | 21/58 |
| 4,011,941 | 3/1977 | Parsons | 202/203 |
| 4,084,747 | 3/1978 | Alliger | 252/187.21 |
| 4,104,190 | 8/1978 | Hartshorn | 252/187.12 |
| 4,456,510 | 2/1984 | Murakami et al. | 204/237 |
| 4,496,452 | 1/1985 | Bianchi | 424/661 |
| 4,499,077 | 2/1985 | Stockel et al. | 424/149 |
| 4,557,925 | 12/1985 | Lindahl et al. | 424/19 |
| 4,568,517 | 2/1986 | Kaspar et al. | 422/30 |
| 4,614,549 | 9/1986 | Ogunbiyi et al. | 435/264 |
| 4,654,208 | 3/1987 | Stockel et al. | 424/78 |
| 4,689,169 | 8/1987 | Mason et al. | 252/187.23 |
| 4,689,215 | 8/1987 | Ratcliff | 424/53 |
| 4,690,773 | 9/1987 | Ogunbiyi | 252/174.12 |
| 4,767,559 | 8/1988 | Kruse et al. | 252/106 |
| 4,792,442 | 12/1988 | Ratcliff | 424/53 |
| 4,855,135 | 8/1989 | Ratcliff | 424/127 |
| 4,861,514 | 8/1989 | Hutchings | 252/187.23 |
| 4,986,990 | 1/1991 | Davidson et al. | 424/665 |
| 5,078,908 | 1/1992 | Ripley et al. | 252/187.21 |

FOREIGN PATENT DOCUMENTS

| | | |
|---|---|---|
| 0082798 | 6/1983 | European Pat. Off. |
| 0147100 | 7/1985 | European Pat. Off. |
| 0196075 | 1/1986 | European Pat. Off. |
| 0209071 | 1/1987 | European Pat. Off. |
| 025504A1 | 5/1988 | European Pat. Off. |
| 0278224 | 8/1988 | European Pat. Off. |
| 3626082A | 11/1988 | Fed. Rep. of Germany |
| WO8504107 | 9/1985 | PCT Int'l Appl. |
| WO8605695 | 10/1986 | PCT Int'l Appl. |
| 2139260A | 11/1984 | United Kingdom |
| 2173017A | 10/1986 | United Kingdom |
| 2151039A | 7/1988 | United Kingdom |

OTHER PUBLICATIONS

Chemical Abstracts Selects: Issue 2, 1987.
Eudragit L Data Sheet (Info L-2/e).

*Primary Examiner*—Richard D. Lovering
*Assistant Examiner*—Joseph D. Anthony
*Attorney, Agent, or Firm*—Frank J. Uxa

[57] ABSTRACT

A method for disinfection a device such as a contact lens. The method comprises contacting the device with an aqueous liquid medium containing an effective amount of chlorine dioxide at effective disinfecting conditions. The chlorine dioxide being derived by contacting a liquid medium containing chlorine dioxide precursor with a transition metal component in an effective amount to promote the generation of chlorine dioxide from the chlorine dioxide precursor. The liquid medium further optionally containing a buffer component in an amount effective to maintain the liquid medium at a desired pH during the generation of chlorine dioxide, and to increase the rate of chlorine dioxide generation from chlorine dioxide precursor relative to a similar liquid medium without the buffer component.

20 Claims, No Drawings

METHODS FOR GENERATING CHLORINE DIOXIDE AND COMPOSITIONS FOR DISINFECTING

This application is a continuation of application Ser. No. 765,219, filed Sep. 24, 1991 now abandoned which, in turn; is a division of application Ser. No. 416,074 filed Oct. 2, 1989, now U.S. Pat. No. 5,078,908.

SCOPE OF THE INVENTION

This invention relates to a method for generating chlorine dioxide from a stable precursor by means of a transition metal. The chlorine dioxide thus generated can be used to disinfect solutions and devices, particularly contact lens solutions and contact lenses.

BACKGROUND OF THE INVENTION

Chlorine dioxide has been found to act as a disinfecting agent. It may have application in disinfecting or sterilizing solutions and devices to which they are applied. This technology has been found to be particularly useful when applied to contact lens solutions and contact lenses.

Contact lenses should be periodically disinfected to protect the wearer's eyes from infection and to improve the wearer's comfort. It is often desirable that lens disinfecting be accomplished quickly, e.g., for the convenience of the wearer. However conventional fast-acting disinfectants that are used with contact lenses have a high potential to cause eye irritation. Fast-acting disinfectants, such as hydrogen peroxide, cause a significant ocular irritation if placed directly in the eye. Thus, when using such disinfectants, a thorough rinsing and/or neutralization step is required to remove substantially all traces of the disinfectant. Also, such disinfectants are often not stable and tend to lose their potency over time. A fast-acting, stable lens disinfecting system which is not as prone to cause eye irritation would clearly be advantageous.

In addition to disinfecting contact lenses, they should also be cleaned of protein-based debris periodically. Such lens cleaning is done using proteolytic enzymes. See for example, Karageozian U.S. Pat. No. 3,910,296.

New compositions and methods for disinfecting devices, particularly contact lenses, have been discovered. These compositions and methods utilize the controlled formation of chlorine dioxide from a precursor by a transition metal, thought to be a catalytic process. The ability to control the formation of chlorine dioxide allows one to effectively and efficiently ship and store the chlorine dioxide as an inactive precursor prior to use. Then, substantially on demand, the precursor is activated or promoted to form or provide a disinfecting amount of chlorine dioxide.

An additional benefit of being able to control the formation or release of the chlorine dioxide is that it allows one to sequentially clean the lens using an enzymatic cleaner and then disinfect the lens in a one step process. This is very convenient for the ultimate user, especially a contact lens wearer, and provides the wearer with an easy and time effective way to maintain his or her lenses. The contact lens wearer experiences more comfort and less irritation because his/her contact lenses are more apt to be clean and disinfected.

SUMMARY OF THE INVENTION

This invention relates in part to a method for generating chlorine dioxide in an aqueous medium, which method comprises buffering the medium to between pH 6-10, and exposing a stable chlorine dioxide precursor to a transition metal for at least one minute.

In one aspect, this invention relates to a composition for generating chlorine dioxide which comprises an aqueous medium, a compound capable of generating chlorine dioxide when exposed to a transition metal, and a transition metal which can catalytically generate chlorine dioxide from said compound in an aqueous medium at a pH between 6-10.

Secondly, this invention relates to an aqueous composition having a pH between 6-10 for disinfecting a device which comprises a compound capable of generating chlorine dioxide when exposed to a transition metal in an aqueous medium and a transition metal which can catalytically generate chlorine dioxide from said compound wherein about at least 0.1 ppm (0.1 mg per liter) of chlorine dioxide is generated.

Furthermore, there is disclosed a tablet comprising a compound capable of generating chlorine dioxide in an aqueous medium when exposed to a transition metal, and a transition metal which can catalytically generates chlorine dioxide from said compound in an aqueous medium at a pH between 6-10, and buffering agents capable of maintaining a pH of between 6-10, wherein said tablet contains sufficient compound to release about at least 0.1 ppm of chlorine dioxide.

Additionally, disclosed is a tablet for cleaning and disinfecting contact lenses comprising a proteolytic enzyme in an amount between 0.0003 and 0.5 Anson units, and a compound capable of generating chlorine dioxide when exposed to a trasition metal in an aqueous medium in an amount sufficient to generate about at least 0.1 ppm of chlorine dioxide, and optionally a transition metal, and buffering agents to maintain the pH between 6-10.

In yet another aspect, there is disclosed a method for generating chlorine dioxide in an aqueous medium, which method comprises buffering the medium to between pH 6-10, and exposing a chlorite compound or a stabilized chlorine dioxide to a transition metal for at least one minute.

DETAILED DESCRIPTION OF THE INVENTION

In its broadest aspect, the invention involves a method and composition for disinfecting a device of any sort. The device to be disinfected is contacted with a composition including an aqueous medium and at least one chlorine dioxide precursor. This contacting takes place in the presence of at least one appropriate transition metal, present in an amount sufficient to facilitate or effect formation of a disinfecting amount of chlorine dioxide from the precursor compound. This contacting results in the device being disinfected. The composition may include buffer components in an amount effective to maintain the pH of the medium in a suitable or desirable pH range during formation of chlorine dioxide from the precursor. It has been found that certain buffers also provide for increases in the rate and/or amount of chlorine dioxide formed from the precursor.

In another broad aspect of the invention, a formulation is provided which contains an enzyme for cleaning accretions and an appropriate metal for activating or promoting release of chlorine dioxide from the stable precursor compound. This embodiment is most applicable to contact lenses. The lenses are exposed to one or more enzymes capable of removing debris from a contact lens in an amount effective to substantially remove debris from the lens and chlorine dioxide generated by this activator/promoter and the stable chlorine dioxide source. What is envisioned is a one pot system where the enzyme and chlorine dioxide are placed in a vial and effect their action without the operator having to take any further action. While the chlorine dioxide can be generated contemporaneously with treating the lenses with an enzyme, it is preferred to conduct the cleaning step and disinfecting step in series. In other words, it is preferred to have one action be effected before the other action. For example the cleaning is effected by the enzyme before the chlorine dioxide is generated, of vice-versa.

Any enzyme can be used in conjunction with this just described process. Proteolytic enzymes are preferred, but lipases or other enzymes which hydrolyze carbohydrates, mucins or other debris which accumulates on surfaces such as contact lenses may be used.

In one embodiment of the foregoing cleaning and disinfecting concept, an aqueous medium is provided which includes the chlorine dioxide precursor and the enzyme. The metal component may be present during the enzyme cleaning in a substantially inactive form. If the enzyme, precursor and metal component are all present during the enzyme cleaning, it is preferred that either the precursor or the metal component be present in a substantially inactive form. This will reduce or eliminate any deleterious or untoward effects the chlorine dioxide precursor or chlorine dioxide may have on enzymatic activity. For example, the precursor or the transition metal component may be present in a delayed release form, in a tablet or pill, together with the enzyme. The enzyme is released substantially immediately on the tablet or pill being submerged in the aqueous medium. The enzyme itself may be present in the tablet or pill, in a delayed release form. After submersion in the liquid medium, the enzyme is released first. After sufficient time for effective enzymatic cleaning of the lens has elapsed, at least 15 minutes or more, the precursor and the transition metal are released. This causes formation of chlorine dioxide and results in disinfecting the enzymatically cleaned lens. This process can be reversed, that is the chlorine dioxide can be generated, then after some discrete time, the enzyme is released into the solution for cleaning purposes.

As applied to lens cleaning and disinfecting, it is envisioned both will take place in a single step in a single pot which does not have to be opened or acted on in order to effect both cleaning and disinfecting. The lens wearer does not need to closely monitor the process or change solutions between the cleaning and disinfecting steps. Overall, the present invention is very easy and effective to use. This encourages compliance with recommended lens care regimens.

The use of the chlorine dioxide generated by this invention is applicable to disinfecting all types of contact lenses. Such lenses may be made of any material or combination of materials and may have any suitable configuration. For example, these solutions and compositions can be used to disinfect lenses made from hydrogels ("soft" lenses), lenses made from polymethyl methacrylate (PMMA), the so called "hard" lenses and other non-hydrogel gas permeable lenses. Present day examples or non-hydrogel gas permeable lens materials are oraganosiloxane-methyacrylate polymers (Polycon ® lenses), fluorocarbon polymers (Advent ® lenses), cellulose acetate butyrate (CAB) materials and silicone elastomer of various compositions. But this invention has applicability to all contact lenses regardless of their chemical composition.

When the appropriate materials and amounts of materials are combined, sufficient chlorine dioxide will be generated to disinfect a given device or solution in a given period of time. Such materials and amounts will be those which in combination generate about at least 0.1 ppm of chlorine dioxide, more preferably about 0.2 ppm, most preferably 0.5 ppm. The amount of chlorine dioxide, when present in solution, will disinfect the solution or the device to which it is applied in about 1 to 2 hours, or less. Higher amounts of chlorine dioxide will disinfect in a shorter period of time.

In general, the chlorine dioxide precursors referred to herein above are compounds capable of generating, releasing or being converted to, chlorine dioxide when exposed to a transition metal. Preferred compounds are those which produce chlorine dioxide in response to increasing acidity. Thus, in mildly acidic conditions, in particular at a pH of less than about 6 and especially in the range of about 3 to 5, the rate of production of chlorine dioxide of these compounds is increased relative to a rate of chlorine dioxide production at neutral pH.

Among the preferred precursor compounds useful in the present invention are chlorites and stabilized chlorine dioxide complexes. The term "stabilized chlorine dioxide" as used herein means, for example, one or more chlorine dioxide-containing complexes disclosed in U.S. Pat. Nos. 4,696,811 and 4,689,215 which are incorporated herein by reference. Chlorites include metal chlorite salts, particularly alkali metal chlorites. A specific example of a chlorite salt which is useful as a chlorine dioxide precursor is sodium chlorite. Among the preferred stabilized chlorine dioxide complexes are carbonate and bicarbonate complexes. The exact chemical composition of many of these stabilized chlorine dioxide precursors is not completely understood. The manufacture or production of certain chlorine dioxide precursors is described in McNicholas U.S. Pat. No. 3,278,447, which is hereby incorporated in its entirety by reference herein. An especially useful stabilized chlorine dioxide is a product sold by Bio-Cide International, Inc. under the trademark PUROGENE.

The chlorine dioxide precursor will be present in the aqueous medium at a predetermined concentration so as to provide a disinfecting amount of chlorine dioxide in the presence of the promoting component. Preferably, the liquid medium has sufficient chlorine dioxide precursor so as to have a potential of producing chlorine dioxide about 0.1 ppm.

In one embodiment, the chlorine dioxide precursor includes a functionality selected from carbonate, borate, sulfate, phosphate, and mixtures thereof. Without intending to limit the scope of the present invention to any particular theory of operation, the inclusion of such groups in the chlorine dioxide precursor may correspond or be analogous to the effect of certain buffer components, as is discussed hereinafter. But the invention is fully operable without reference to a specific buffer.

Any transition metal capable of effecting the release of chlorine dioxide from the precursor in an aqueous medium at a pH between 6-10, or possibly higher, may be employed as a promoter in the present invention. The primary criteria for such transition metal is that it have the ability to effect formation of a disinfecting amount of chlorine dioxide from the described chlorine dioxide precursors. Such metals should also have no substantial detrimental effect on the lens to be disinfected.

It is preferred that the metal component be present as a solid. In certain embodiments, solid metals can be easily and conveniently introduced into or removed from the chlorine dioxide precursor-containing liquid medium, as desired. Also a solid metal component can be readily separated from the solution for repeated use in disinfecting lenses. The metal may be immobilized, or maintained substantially stationary, relative to the solution.

The particular metals of interest herein are the transition metals and mixtures thereof, in particular from Group III metals, Group IV metals, Group V metals, Group VI metals, Group VII metals, Group VIII metals and mixtures thereof.

Because of their high degree of effectiveness, platinum group metals and mixture thereof, and especially platinum, are particularly useful. The platinum group metals include platinum, palladium, iridium, ruthenium, rhodium and osmium.

The metal or metals may be present in the metallic form and/or in a combined form as part of an organic or inorganic compound or complex.

The amount of metal needed to practice this invention is to be viewed in terms of what quantity or surface area is useful to generate a particular concentration of chlorine dioxide in a given time and in light of the amount of precursor present in solution. It has been observed that the metal is not used up in the process of generating chlorine dioxide. Thus it is assumed the metal acts as a catalyst to effect formation of the chlorine dioxide. But the chemistry has not been investigated other than to observe that the metal apparently is not consumed in the process of creating chlorine dioxide.

Assuming the process is catalytic in nature, the amount of metal surface area exposed to the solution should be taken into consideration. Specific surface area data can be readily determined by simply exposing a chlorite salt of one concentration to various metals deposited on different surface areas, then observing the rate of chlorine dioxide formation. From there, actual working parameters can be generated. Transition metals useful herein can also be dispersed in the aqueous medium.

It is most convenient to plate the metals on some support device. Such supports are particularly useful if the metal includes one or more platinum group metals, which are quite expensive. The support may be chosen so as to provide surface area on which the promotion component can be placed.

Any suitable support material may be employed, and preferably is substantially inert at the conditions employed in the present invention. Examples of support materials include polymeric materials (plastics), metals, aluminas, silicas, clays, ceramics and the like. The supported promotion component may have any suitable shape or configuration, such as sheets, rods, extrudates, tablets, pills, irregular shaped particulars, spheres, disks and the like. Any of a number of conventional techniques can be employed to deposit the metal-containing component on the support material. These techniques include impregnation, co-precipitation, ion-exchange, dipping, spraying, vacuum depositions and the like.

The aqueous medium used is selected to have no substantial detrimental effect on the lens being treated and to allow and preferably to even facilitate the present lens treatment or treatments. If the devices being disinfected are contact lenses, a particularly useful aqueous medium is saline, for example, a saline solution conventionally used for wetting and storing contact lenses.

During the disinfecting contacting, it is preferred that the aqueous medium have a pH in the range of about 6 to 10, but more preferably about 7.5. Such more preferred pH ranges are substantially consistent with the normal physiological pH for humans. Thus, after disinfecting, the disinfected lens may be placed directly in the eye.

This invention may be practiced at a pH lower than 6. At that pH, and lower, chlorine dioxide is generated from chlorites and many stabilized chlorine dioxides by virtue of the lower pH. In essence, the precursor is not stable for very long at these lower pHs at standard temperature and pressure. So formulating a composition for use at some remote time such as is often encountered with consumer products where the shelf life of the product must be many months means this aspect of the invention has certain formulation limitations. But it has been found that a transition metal will increase the amount of chlorine dioxide generated at lower pHs, as well as the rate at which it is generated. Thus, disinfecting in the presence of transition metal and chlorine dioxide precursors under relatively highly acidic conditions is within the scope of the present invention. If such highly acidic conditions are employed, a neutralization step may be useful to neutralize any acidic residue which may remain in or on the device. Neutralization can be easily accomplished by rinsing or soaking the disinfected device in a neutral or slightly basic saline solution.

The disinfecting contacting preferably occurs at room temperature, but may be practiced at mildly elevated temperatures, up to 40° C. or there abouts. This contacting preferably occurs for a time to substantially completely disinfect the lens being treated. Such contacting times can be in the range of about 5 minutes to about 2 hours or more depending on the concentration of chlorine dioxide generated in the medium.

In order to ensure that the pH of the aqueous medium is maintained within the desired range during the disinfecting procedure, the liquid aqueous medium may include at least one buffer component. Although any suitable buffer component may be employed, it is preferred to select such component so as not to substantially detrimentally affect the desired formation of chlorine dioxide. It is preferred that the buffer component be inorganic.

Among the preferred buffer components are those which include phosphate functionalities, borate functionalities, carbonate functionalities and mixutres thereof. Particularly increased rates of chlorine dioxide formation are achieved when the buffer component includes phosphate functionalities, borate functionalities and mixtures thereof. Alkali metal and alkaline earth metal salts of these buffer components are advantageously used in the present invention.

In another embodiment, a composition is provided which includes an aqueous medium, at least one chlorine dioxide precursor capable of generating chlorine dioxide when exposed to a transition metal, a transition metal and an enzyme. This composition or formula is useful for effecting a one-step cleaning and disinfecting of devices such as contact lenses. By one-step it is meant that the cleaning and disinfecting occurs in one vessel without changing solution. Preferably, this is accomplished sequentially. For example, one can provide the enzyme to the solution and then generate the chlorine dioxide or provide the enzyme to the same solution after disinfection has been accomplished. The liquid aqueous medium and chlorine dioxide precursor and promoter are described elsewhere herein.

The enzyme or enzymes used are capable of removing debris from a device such as a contact lens. The amount of such enzyme or enzymes used (included in the present composition), protein, lipoproteins, lipids, mucins or saccharide should be effective to remove substantially all of the debris from a device such as a contact lens in a reasonable time, preferably in the range of about 5 minutes to 12 hours. The active enzyme-containing liquid medium preferably contains sufficient enzyme to provide between about 0.001 to about 5 Anson units of activity, more preferably between about 0.01 to about 1 Anson units, per single lens treatment. In weight/volume terms, since enzyme preparations are seldom pure, it is expected that the enzyme source will be used in amounts between about 0.003 to 15% w/v of the final working solution. The precise amount will vary with the purity of the enzyme and will need to be finally determined on a lot-by-lot basis.

The enzyme employed may be selected from enzymes which may be employed in the enzymatic cleaning of contact lenses. These include proteases, lipases, amylases, mucolytic enzymes or the like. Reference is made to the compendium enzyme titles, "Enzyme Nomenclature," 1984, Ed. E. C. Webb, Academic Press, Inc., New York (1984). Any one or more of these enzymes may be used in this invention as is appropriate and safe for removing soils from devices. Where contact lenses are concerned, protein and mucin buildup are two types of soils readily removed by enzymes. Hence, preferred formulations here include at least one protease and may contain mucolytic enzymes as well. For example, many of the enzymes disclosed in Huth et al. U.S. Pat. No. Re. 32,672 are useful in the present invention.

It is preferred that the cleaning action of the enzyme or enzymes occur prior to the chlorine dioxide disinfecting of the lens. This is so because the chlorine dioxide may inactive or destroy the enzyme before cleaning has occured. To effect this, the transition metal can be added to or combined with the composition after the desired enzymatic cleaning has occured. But the compound from which the chlorine dioxide is generated may be present in the solution at the time enzymatic cleaning is desired, or may be effectively delayed in its introduction into the solution either by adding a separate formulation or by encapsulating this compound in a delayed release formulation.

In another embodiment, the transition metal is included in the composition in a substantially non-promotional form, preferably in a delayed release form. For example, the enzyme and the chlorine dioxide precursor and/or the metal may be present together in tablet or pill. As the tablet or pill is combined with the aqueous medium, the enzyme is released first and becomes available to remove debris from the to-be-cleaned lens. During this time, when the enzyme is cleaning the lens, the chlorine dioxide precursor and/or the metal-containing component preferably both remain in the tablet or pill, effectively out of contact with the solution containing the enzyme during the cleaning phase of the lens treatment. After a period of time during which the enzyme effects a cleaned device, the chlorine dioxide precursor and the metal are introduced into the solution. This causes chlorine dioxide to form which, in turn, results in disinfecting the lens. Thus, a single tablet or pill can be used to both clean and disinfect the lens. It is preferred that the tablet contain the enzyme, chlorine dioxide precursor and transition metal. In another useful embodiment, where no lens cleaning is desired, the tablet or pill contains just the chlorine dioxide precursor and transition metal. This tablet or pill, after being introduced into the solution, forms a lens disinfecting amount of chlorine dioxide.

Although multi-layered (including core and coating layering) tablets or pills are preferred, the delayed release form of the present components can be present in any other suitable item or items, such as masses of powders, granules and the like. Delayed release technology is well known in the art as exemplified by the text *Controlled Drug Delivery*, 2nd Ed., Joseph R. Robinson and Vincent H. L. Lee, Eds., Marcel Dekker, Inc., New York, 1987.

Items which release their ingredients in a sequential, time delayed manner are well known and can be produced using conventional technology. Therefore, a detailed description of such items and such production technology is not presented here. However, such items are preferably designed to allow the enzyme or enzymes sufficient time to remove at least a major amount, and more preferably substantially all, of the debris from the lens. In other words, such components are preferably designed so that sufficient time elapses between release of the enzyme and formation of chlorine dioxide to allow the enzyme to perform its cleaning function. Such sufficient time is preferaby in the range of about 1 minute to about 6 hours, more preferably about 15 minutes to about 2 hour. Thirty to sixty minutes may also effectively clean and disinfect lenses using these embodiments.

In one useful embodiment, the transition metal is incorporated into a lens disinfecting system. This system comprises a chamber adapted and sized to hold the lens to be disinfected, and a solution containing at least one chlorine dioxide precursor in an amount adequate upon exposure to the transition metal to produce sufficient chlorine dioxide to disinfect the lens. A support containing the transition metal is secured to the chamber and includes at least one solid transition metal component in an amount to effect formation of sufficient chlorine dioxide from the chlorine dioxide precursor to disinfect lenses. The transition metal may be one or more of the transition metals described above.

The following examples illustrate certain aspects of the present invention.

EXAMPLE 1

This example illustrates the effect of stabilized chlorine dioxide concentration on the production of chlorine dioxide.

A series of solutions was prepared using different concentrations of a stabilized chlorine dioxide product, sold by Bio-Cide International, Inc. under the trademark Purogene ®. The stabilized chlorine dioxide product included 2.0% by weight of potential (ultimate yield) chlorine dioxide and 0.085% by weight of sodium carbonate.

Each of these solutions was prepared as follows:
(1) 0.1% (W/V) of boric acid was dissolved in deionized water to provide buffering;
(2) a calculated amount of sodium chloride was added so that the final solution was isotonic;
(3) the pH of the solution was adjusted to 7.5%;
(4) the desired amount of the stabilized chlorine dioxide product was added; and
(5) the final volume of the solution was adjusted using deionized water.

Each of these solutions was tested as follows. A 10 ml. aliquot of the solution was placed in a plastic container at ambient temperature and pressure. A plastic disc containing platinum as platinum oxide was placed in the solution. The concentration of chlorine dioxide was monitored as a function of time after the disc was placed in the container.

Results of these tests are given in Table 1.

TABLE 1

| Time | Starting Conc. of precursor (PPM) | | | | | | |
|---|---|---|---|---|---|---|---|
| | 0.0 | 50 | 100 | 250 | 500 | 750 | 1000 |
| 0 | 0.0 | 0.00 | 0.00 | 0.00 | 0.00 | 0.00 | 0.00 |
| 30 | 0.0 | 0.74 | 0.99 | 1.80 | 3.76 | 6.40 | 6.31 |
| 60 | 0.0 | 0.94 | 1.61 | 5.11 | 6.11 | 8.19 | 10.79 |
| 90 | 0.0 | 1.09 | 1.66 | 3.72 | 10.92 | 8.46 | 12.28 |
| 120 | 0.0 | 0.90 | 1.81 | 4.06 | 12.08 | 11.80 | 12.78 |
| 240 | 0.0 | 1.13 | 1.26 | 4.95 | 8.10 | 11.18 | 19.19 |
| 480 | 0.0 | 1.00 | 1.28 | 4.08 | 5.17 | 10.23 | 13.78 |

EXAMPLES 2 AND 3

Two series of solutions were prepared for testing. One set of solutions contained 1000 ppm by weight of the stabilized chlorine dioxide as identified in Example 1 and varying concentrations of sodium chloride and borate buffer. The second set of solutions contained 1030 ppm. by weight of technical grade sodium chlorite and varying concentrations of sodium chloride and borate buffer. This technical grade sodium chlorite contained: 80% by weight $NaClO_2$, 3% by weight NaCl, 5% by weight $Na_2CO_3$, 2% by weight $NaClO_3$.

Each of these solutions was tested in accordance with the procedure outlined in Example 1. The chlorine dioxide concentration of each aliquot was determined after 30 minutes exposure to the platinum disc. The pH was 7.5 for all solutions.

Results of these tests were as follows:

TABLE 2

| | NaCl wt % | Borate Buffer, wt % | $ClO_2$ ppm. by wt. | No Disc Control |
|---|---|---|---|---|
| EXAMPLE 2 - Stabilized Chlorine Dioxide Product (SCDP) | | | | |
| SCDP, ppm. by wt. | | | | |
| 1000 | 0.0 | 0.0 | 1.61 | 0.00 |
| 1000 | 0.7 | 0.0 | 1.41 | 0.00 |
| 1000 | 0.0 | 0.1 | 6.51 | 0.00 |
| 1000 | 0.7 | 0.1 | 6.31 | 0.00 |
| EXAMPLE 3 - Technical Grade Sodium Chlorite (TGSC) | | | | |
| TGSC, ppm. by wt. | | | | |
| 1030 | 0.0 | 0.0 | 1.28 | 0.00 |
| 1030 | 0.7 | 0.0 | 1.49 | 0.00 |
| 1030 | 0.0 | 0.1 | 7.29 | 0.00 |
| 1030 | 0.7 | 0.1 | 7.12 | 0.00 |

EXAMPLE 4

Another series of aqueous solutions was prepared using the same concentration of the stabilized chloride dioxide product as identified in Example 1 together with varying concentrations of boric acid. Each of these solutions was tested in accordance with the procedure outlined in Example 1. The chlorine dioxide concentration of each aliquot was determined after 30 minutes exposure to the platinum disc.

Results of these tests were as follows:

TABLE 3

| Boric Acid, wt. % | $ClO_2$, ppm. by wt % | No Disc Control |
|---|---|---|
| 0.00 | 2.10 | 0.00 |
| 0.025 | 4.36 | 0.00 |
| 0.050 | 5.36 | 0.00 |
| 0.100 | 6.32 | 0.00 |
| 0.150 | 7.22 | 0.00 |
| 0.200 | 7.50 | 0.00 |
| 0.250 | 9.62 | 0.00 |
| 0.300 | 10.30 | 0.00 |
| 0.400 | 11.20 | 0.00 |
| 0.500 | 11.23 | 0.00 |
| 0.600 | 11.29 | 0.00 |
| 0.800 | 11.38 | 0.00 |

These results show that chlorine dioxide production increased with increasing boric acid concentrations up to a boric acid concentration of about 0.4% by weight. From 0.4% to 0.8% by weight of boric acid, the concentration of chlorine dioxide remained substantially unchanged.

EXAMPLE 5

A further series of aqueous solutions was prepared with each solution having the same concentration of the stabilized chlorine dioxide product as identified in Example 1 and substantially the same concentration of sodium chloride. Each solution also included a substantially similar concentration (on a molar basis) of a different buffer. A baseline solution with no added buffer was also prepared. The pH of each solution was maintained at about 7.5 throughout the testing. Each of these solutions was tested in accordance with the procedure outlined in Example 1. The chlorine dioxide concentration of each solution was determined after 30 minutes exposure to the platinum disc.

Results of these tests are given in Table 4.

TABLE 4

| Buffer | Buffer Concen. molarity, wt % | NaCl, wt % | With Disc $ClO_2$ ppm by wt | Control (No Disc) |
|---|---|---|---|---|
| none | — | — | 0.70 | 1.41 | 0.00 |
| TRIS | 0.020 | 0.242 | 0.67 | 0.16 | 0.00 |
| carbonate | 0.020 | 0.212 | 0.60 | 5.35 | 0.00 |
| boric acid | 0.160 | 0.100 | 0.70 | 6.31 | 0.00 |
| phosphate | 0.020 | 0.276 | 0.63 | 6.80 | 0.00 |

The rate of chlorine dioxide generation from Purogene can be affected by the particular buffer if one is used in maintaining the pH of these solutions. The use of the TRIS buffer appears to have a negative effect on $ClO_2$ release in this study.

EXAMPLE 6

A series of aqueous solutions was prepared using 1000 ppm of the stabilized chlorine dioxide product set out in Example 1. Varying amounts of sodium chloride were added to determine the effect of ionic strength on chlorine dioxide production. Each of these solutions was tested in accordance with the procedure outline in Example 1. The chlorine dioxide concentration of each aliquot was determined at 30 minutes.

Results of these tests are given in Table 5.

TABLE 5

| NaCl, wt % | ClO$_2$ ppm. by wt | No Disc Control |
|---|---|---|
| 0.0 | 7.62 | 0.00 |
| 0.1 | 6.99 | 0.00 |
| 0.4 | 6.96 | 0.00 |
| 0.7 | 7.14 | 0.00 |
| 1.0 | 7.06 | 0.00 |
| 1.3 | 6.88 | 0.00 |
| 1.3 | 6.80 | 0.00 |

These results indicate that the ionic strength of the solution had little effect on the production of chlorine dioxide. As sodium chloride content was increased from 0.0% to 0.1% by weight, there was a 9% drop in chlorine dioxide production. Further increases in ionic strength did not substantially affect chlorine dioxide production.

EXAMPLE 7

Three aqueous solutions containing the same concentration, 50 ppm. by weight, of the stabilized chlorine dioxide product identified in Example 1 were prepared. The solutions also included 0.1% by weight of boric acid and 0.85% by weight of sodium chloride. Each of these solutions had a different pH and was tested in accordance with the procedure outlined in Example 1. The chlorine dioxide concentration of each aliquot was determined after 30 minutes exposure to the platinum-containing disc.

Results of these tests are given in Table 6.

TABLE 6

| pH | No Disc (ClO$_2$) | ClO$_2$ Concentration, ppm. by wt. |
|---|---|---|
| 7.9 | 0.00 | 1.10 |
| 7.5 | 0.00 | 2.35 |
| 6.8 | 0.00 | 3.42 |

There was approximately three (3) times as much chlorine dioxide produced at pH 6.8 as at pH 7.9.

EXAMPLE 8

Two solutions containing 50 ppm of the stabilized chlorine dioxide product identified in Example 1 were prepared. One solution had a pH of 6.5 and the other solution had a pH of 6.0. Each of these solutions was monitored for chlorine dioxide concentration both with and without the platinum-containing disc described in Example 1.

Results of these tests are set out in Table 7

TABLE 7

| Time Minutes | pH - 6.0 ClO$_2$ Concentration, ppm. by wt. | | pH - 6.5 ClO$_2$ Concentration, ppm. by wt. | |
|---|---|---|---|---|
| | No Disc | Disc | No Disc | Disc |
| 0 | 0.944 | 0.944 | 0.023 | 0.023 |
| 30 | 0.601 | 2.547 | 0.094 | 1.105 |
| 90 | 0.338 | 2.523 | 0.039 | 1.170 |
| 120 | 0.318 | 1.984 | 0.258 | 1.227 |

These results indicate that platinum oxide increases the production of chlorine dioxide even as the pH is lowered. Thus, it may be advantageous to contact the lens to be disinfected with the chlorine dioxide precursor in the presence of a metal-containing component at a pH lower than the normal human physiological range. This treatment may involve a subsequent neutralization step in order to ready the disinfected lens for wear.

EXAMPLE 9

Various platinum discs were selected for testing. Each of the discs had a different geometric surface area. The solution used in this testing include 200 ppm by weight of the stabilized chlorine dioxide product identified in Example 1. Each of these discs was tested in accordance with the procedure outlined in Example 1. The chlorine dioxide concentration of each aliquot was determined after 30 minutes exposure to the platinum disc.

Table 8 sets out these results.

TABLE 8

| Surface Area cm$^2$ | ClO$_2$ Concentration, ppm. by wt. |
|---|---|
| 2.50 | 0.32 |
| 3.50 | 0.63 |
| 5.30 | 0.72 |
| 5.57 | 0.70 |
| 5.73 | 0.63 |
| 6.00 | 1.04 |
| 11.30 | 1.83 |
| 11.30 | 2.14 |
| 11.30 | 1.50 |
| 16.87 | 2.62 |
| 22.60 | 2.73 |

These results demonstrate that as the geometric surface area of the disc increased past 11.3 cm$^2$, the production of chlorine dioxide continued to increase, but at a slower, non-linear rate.

EXAMPLE 10

Aluminum pellets coated with ruthenium oxide and having a surface area of about 7.9 cm$^2$ were selected for testing. These pellets were exposed to an aqueous solution of 200 ppm of the stabilized chlorine dioxide product for 30 minutes using the same container as in Example 1. The concentration of chlorine dioxide was monitored.

The average amount of chlorine dioxide produced per cm$^2$ of ruthenium-containing pellet surface area was about 0.080 ppm. The comparable average amount of chlorine dioxide produced per cm$^2$ of platinum-containing disc surface area was about 0.146 ppm. The control solution with no disc produced 0.00 ppm ClO$_2$. Although the ruthenium oxide pellets were not as effective as the platinum oxide disc, it is believed that ruthenium oxide pellets are useful in the present invention, particularly if higher surface area pellets are employed and the amount of chlorine dioxide precursor is increased.

EXAMPLE 11

A solution containing deionized water, 0.85% (w/v) of sodium chloride, 0.10% (w/v) of boric acid, and 50 pp. w/v of the stabilized chlorine dioxide product identified in Example 1 was prepared. One portion of this solution was buffered to a pH of 7.9, while the other portion was buffered to a pH of 6.8. Varying amounts of tartaric acid was added to different aliquots of each of these portions. The aliquots were then tested, following the standard procedure, to determine the D-value with respect to various microorganisms. The D-value is defined as the length of time required to reduce the microbial burden or load by one log unit.

Results are given in Table 9.

TABLE 9

| Microorganisms | Extrapolated D-value at 23° C. min. | | | | |
|---|---|---|---|---|---|
| | Tartaric Acid, ppm. | | | | |
| | 30 | 40 | 50 | 60 | 70 |
| | Free Chlorine Dioxide, ppm | | | | |
| | 10.74 | 17.08 | 37.94 | 25.38 | 32.47 |
| | pH = 6.8 | | | | |
| S. marcescens | <0.84 | <0.84 | <0.84 | <0.84 | <0.84 |
| S. aureus | <0.87 | <0.87 | <0.87 | <0.87 | <0.87 |
| P. aeruginosa | <0.85 | <0.85 | <0.85 | <0.85 | <0.85 |
| A. fumigatus | <0.83 | <0.83 | <0.83 | <0.83 | <0.83 |
| | Tartaric Acid, ppm. | | | | |
| | 30 | 40 | 50 | 60 | 70 |
| | Free Chlorine Dioxide, ppm | | | | |
| | 0.03 | 0.11 | 0.05 | 0.15 | 0.23 |
| | pH = 7.9 | | | | |
| S. marcescens | 5.13 | <0.85 | 2.56 | <0.85 | 2.56 |
| S. aureus | 10.17 | 2.54 | 2.54 | 12.24 | 2.54 |
| P. aeruginosa | 19.48 | <0.87 | 2.6 | <0.87 | <0.87 |
| A. fumigatus | 109 | 109 | 150 | 162.2 | 70.6 |

These results indicate that chlorine dioxide in an aqueous solution is effective to disinfect contact lenses. Thus, these results demonstrate that sufficient chlorine dioxide can be provided in a liquid medium to reduce the microbial burden or load by one log order in a period of time generally deemed acceptable for disinfecting contact lenses.

EXAMPLE 12

This example illustrates a lens cleaning and disinfecting embodiment of the present invention.

A protein-based debris laden hydrogel contact lens is placed in a plastic container. A quantity of a saline solution containing 500 ppm by weight of the stabilized chlorine dioxide product identified in Example 1 and 0.3% by weight of boric acid is added to the container. The pH of this solution is about 7.5.

A layered, delayed release tablet is dropped into the solution in the container. The center core of this tablet is a plastic disc which includes a platinum-containing coating. The outer layer of the tablet includes a quantity of a proteolytic enzyme. The layer between the enzyme-containing layer and the platinum coated disc is structured and designed to completely dissolve or destruct in 30 minutes after being exposed to the solution in the container.

Upon being dropped into the solution, the enzyme in the outer layer of the tablet is released and begins to break down the protein-based debris on the lens. In 30 minutes, substantially all of the protein-based debris is removed from the lens, and the platinized disc is exposed to the solution. This exposure results in the production of a disinfecting amount of chlorine dioxide which acts to disinfect the cleaned lens. Throughout this procedure the pH of the solution remains in the physiological range.

Six hours after the tablet is dropped into the solution, the cleaned and disinfected lens is removed from the solution. After a light saline rinse the lens is ready to be placed in the lens wearer's eye.

This cleaning/disinfecting procedure requires only one step as opposed to conventional separate cleaning and disinfecting steps with the need for human intervention between the steps. Thus, the present system is very convenient to use and reduces the amount of time the wearer must actively spend to clean and disinfect his/her lenses.

While this invention has been described with respect to various specific examples and embodiments, it is to be understood that the invention is not limited thereto.

What is claimed is:

1. A method for disinfecting a device which comprises:
   contacting said device with an aqueous liquid medium containing an effective disinfecting amount of chlorine dioxide at effective disinfecting conditions, said chlorine dioxide being derived by contacting a liquid medium containing chlorine dioxide precursor with a transition metal component in an amount effective to promote the generation of chlorine dioxide from said chlorine dioxide precursor, said liquid medium further containing a buffer component in an amount effective to maintain said liquid medium at a desired pH during the generation of chlorine dioxide and to increase the rate of chlorine dioxide generation from said chlorine dioxide precursor relative to a similar liquid medium without said buffer component.

2. The method of claim 1 wherein said device is an ophthalmic device.

3. The method of claim 1 wherein said device is a contact lens.

4. The method of claim 1 wherein said chlorine dioxide precursor is selected from the group consisting of stabilized chlorine dioxide, chlorite salts and mixtures thereof.

5. The method of claim 1 wherein said transition metal component comprises a metal selected from the group consisting of platinum, palladium and ruthenium.

6. The method of claim 1 wherein said liquid medium has a pH in the range of about 6 to about 10, and at least 0.1 ppm by weight, based on the weight of said liquid medium, of chlorine dioxide is generated.

7. The method of claim 1 wherein said buffer component includes at least one functionality selected from the group consisting of phosphate functionalities, borate fuctionalities, carbonate functionalities and mixtures thereof.

8. The method of claim 11 wherein said liquid medium is aqueous-based.

9. The method of claim 8 wherein said aqueous liquid medium includes said liquid medium.

10. A method for treating a contact lens which comprises:
    contacting an aqueous liquid medium containing chlorine dioxide precursor with a transition metal component at conditions effective to generate a contact lens disinfecting amount of chlorine dioxide from said chlorine dioxide precursor and form a chlorine dioxide-containing liquid medium; and
    contacting a contact lens with said chlorine dioxide-containing liquid medium for a sufficient amount of time, thereby disinfecting said contact lens.

11. The method of claim 10 wherein said aqueous liquid medium has a pH in the range of about 6 to about 10.

12. The method of claim 10 wherein said chlorine dioxide-containing liquid medium includes at least about 0.1 ppm by weight of chlorine dioxide.

13. The method of claim 10 wherein said chlorine dioxide precursor is selected from the group consisting of stabilized chlorine dioxide, chlorite salts and mixture thereof.

14. The method of claim 10 wherein said transition metal component comprises a metal selected from the group consisting of platinum, palladium and ruthenium.

15. The method of claim 10 wherein said aqueous liquid medium includes a buffer component in an amount effective to maintain the pH of said aqueous liquid medium in the range of about 6 to about 10.

16. The method of claim 15 wherein said buffer component includes at least one functionality selected from the group consisting of phosphate functionalities, borate functionalities, carbonate functionalities and mixtures thereof.

17. The method of claim 10 which further comprises contacting said contact lens with an effective amount of an enzyme component to remove debris from said contact lens.

18. The method of claim 17 wherein said contact lens/enzyme component contacting occurs either before or after said contact lens/chlorine dioxide-containing liquid medium contacting.

19. The method of claim 17 wherein said enzyme component is selected from the group consisting of proteolytic enzymes and mixtures thereof.

20. A method for disinfecting a contact lens which comprises:

contacting a contact lens with a chloride dioxide-containing liquid medium having a pH lower than 6 to thereby disinfect said contact lens, said chlorine dioxide-containing liquid medium being derived by contacting an aqueous liquid medium containing chlorine dioxide precursor with a transition metal component at conditions effective to generate a contact lens disinfecting amount of chlorine dioxide from said chlorine dioxide precursor; and, thereafter, contacting said contact lens with a neutral or slightly basic saline solution.

* * * * *